United States Patent [19]

Steffan

[11] Patent Number: 4,764,621
[45] Date of Patent: Aug. 16, 1988

[54] PREPARATION OF 2-CHLOROBENZTHIAZOLE

[75] Inventor: Guido Steffan, Odenthal, Fed. Rep. of Germany

[73] Assignee: Bayer Aktiengesellschaft, Leverkusen, Fed. Rep. of Germany

[21] Appl. No.: 526,932

[22] Filed: Aug. 26, 1983

[30] Foreign Application Priority Data

Sep. 17, 1982 [DE] Fed. Rep. of Germany ....... 3234530

[51] Int. Cl.$^4$ .......................................... C07D 277/62
[52] U.S. Cl. ...................................................... 548/152
[58] Field of Search ........................................ 548/152

[56] References Cited

FOREIGN PATENT DOCUMENTS 0039905 11/1981 European Pat. Off. ............ 548/152
0043013 1/1982 European Pat. Off. ............ 548/152
1670453 2/1982 Fed. Rep. of Germany ...... 548/152

OTHER PUBLICATIONS

Eisch, Adv. Heterocycl. Chem. 7, 1–37, (1966).
Ullmanns Encyklopadie der Technischen Chemie, Prof. Dr. Ing S. Balke et al., 1966, pp. 330–331.

Primary Examiner—Robert Gerstl
Attorney, Agent, or Firm—Sprung Horn Kramer & Woods

[57]                ABSTRACT

A process for the preparation of 2-chlorobenzthiazole comprising reacting benzthiazole with elementary chlorine in an inert, boiling solvent in the presence of a catalyst. Advantageously the solvent is phosphorus oxychloride or chlorobenzene, the catalyst is iron-III chloride or aluminum chloride and phosphorus trichloride or pyridine is also present as a co-catalyst. The desired product is obtained in high yield.

6 Claims, No Drawings

PREPARATION OF 2-CHLOROBENZTHIAZOLE

The invention relates to a process for the preparation of 2-chlorobenzthiazole by chlorinating benzthiazole.

2-Chlorobenzthiazole is usually prepared by reacting 2-mercaptobenzthiazole with chlorine, sulphur chlorides, thionyl chloride, phosgene, sulphuryl chloride or similar chlorinating agents (compare Houben-Weyl, Methoden der Organischen Chemie [Methods of Organic Chemistry], 4th Edition, Volume 5/3, pages 858 and 871 (1962); and also J. Amer. Chem. Soc. 68, page 1, 666 (1946); and DE-AS [German Published Specification] No. 1,164,413).

However, these processes do not result in satisfactory yields, and by-products of little use are formed in addition. Although good yields of 2-chlorobenzthiazole are obtained when phosgene is used as the reagent (DE-AS [German Published Specification] No. 1,164,413), carbon oxysulphide, which can scarcely be made use of, is obtained as a by-product.

Additionally, a method for the preparation of 2-chlorobenzthiazoles by reacting 2-chlorophenyl iso-cyanide-dichlorides with sulphur is described in a recent patent application (EP-A1 0,039,905); the starting product required must, however, first be prepared.

The direct chlorination of benzthiazole, which is available on a large industrial scale, appears particularly attractive for the preparation of 2-chlorobenzthiazole on a large industrial scale.

It has not been possible to find literature or patents relating to the direct chlorination of benzthiazole to give 2-chlorobenzthiazole. Accordingly, the direct chlorination of benzthiazole to give 2-chlorobenzthiazole appears not to have been successful hitherto.

Ullmann's "Enzyklopädie der technischen Chemie" ["Encyclopaedia of Industrial Chemistry"], 3rd Edition, Volume 17, page 331 reads as follows:

"In the case of benzothiazole, the substituents (halogen is also intended) enter into the benzene ring, preferably into the 6-position or 4-position."

This statement can be confirmed, in the case of customary chlorination, on the basis of our own tests: a mixture of chlorinated products is formed, the main components of which carry the chlorine on the benzene ring, and which can only be split up with difficulty.

It has now been found, surprisingly, that 2-chlorobenzthiazole is obtained in high yields by direct chlorination of benzthiazole, if benzthiazole is chlorinated with elementary chlorine in an inert, boiling solvent, in the presence of a catalyst and, if appropriate, in the presence of a co-catalyst. Suitable solvents are phosphorus oxychloride ($POCl_3$) and, in particular, chlorobenzene. Suitable catalysts are iron-III-chloride and aluminum chloride; suitable co-catalysts are phosphorus trichloride ($PCl_3$) and pyridine.

Under the conditions according to the invention, the chlorine enters almost exclusively into the desired 2-position of the heterocyclic structure. The structure of 2-chlorobenzthiazole has been confirmed by elementary analysis, IR spectrum, NMR spectrum and determination of the saponifiable chlorine.

The process of the invention may be illustrated in greater detail on the basis of the following equation:

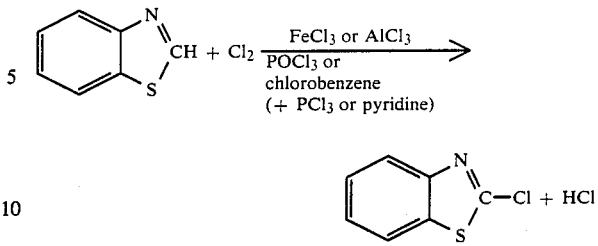

In carrying out the process according to the invention, at least 1 mol of chlorine is employed for 1 mol of benzthiazole. However, in order to achieve as complete a conversion as possible, it is advantageous to employ the chlorine in a slight excess, for example in an excess of up to 20%. It is preferable to employ for the reaction a quantity of chlorine which is about 1.1 times the quantity required by stoichiometry.

The aluminum chloride or iron-III chloride used as the catalyst is employed, in each case, in quantities of about 0.2 to 2 mol%, relative to benzthiazole.

The commencement of chlorination can be facilitated considerably by adding one of the co-catalysts mentioned to the reaction mixture before chlorination is begun; the quantity employed should be approximately equivalent to the quantity of catalyst.

In addition, it is advantageous to maintain a specific program of passing in chlorine: chlorine should be passed in quite slowly at the start, later in a rapid manner and, towards the end, more slowly again.

2-Chlorobenzthiazole is obtained in this procedure in yields of over 90% of theory and can be obtained in purities from 97 to over 99% by distillation.

It is found that the yields tend to become better at a greater dilution with solvent; if the quantity of solvent falls below a specific level, the yields fall off considerably. It is most advantageous to carry out the reaction using quantities of solvent of 180 to 300 ml of phosphorus oxychloride or 200 to 350 ml of chlorobenzene per mol of benzthiazole. It is worthy of note that the chlorobenzene is not chlorinated further under the reaction conditions described to give more highly chlorinated benzenes.

The reaction temperature is given by the boiling point of the solvent used. The reaction is generally carried out under normal pressure.

The 2-chlorobenzthiazole is isolated by distillation from the reaction mixture in a customary manner.

2-Chlorobenzthiazole can be used, for example, as an intermediate product for the preparation of specific herbicides (compare, for example, EP-B1-0,005,501). Thus the known herbicidally active compound benzthiazol-2-yloxyacetic acid N-methylanilide can be prepared by reaction with hydroxyacetic acid N-methylanilide (compare also EP-A1-0,014,409).

The examples which follow are intended to serve as a further illustration of the invention. (The abbreviation GC represents gas chromatogram).

EXAMPLES

Example 1

150 g of chlorine are passed into a mixture of 400 ml of phosphorus oxychloride, 270 g (2 mols) of benzthiazole, 1.7 g of aluminum chloride and 1.7 g of pyridine at the boiling point (115° C.), in the course of 3 hours (vigorous evolution of HCl).

The reaction mixture is stirred for a further hour and is then separated by distillation—partly in vacuo—through a short Vigreux column. This gives:

638 g of first runnings (according to GC: 99.6% of $POCl_3$ and 0.4% of benzthiazole) 316 g of main fraction (according to GC: 0.15% of $POCl_3$, 0.1% of benzthiazole, 98.3% of 2-chlorobenzthiazole and 1.4% unknown) and 34 g of distillation residue.

Yield of 2-chlorobenzthiazole: 91.6% of theory.

Example 2

8 kg of chlorine are passed into a mixture of 1,000 kg of phosphorus oxychloride, 405 kg (3 kmols) of benzthiazole, 3 kg of iron-III chloride and 10 kg of phosphorus trichloride at 115° C. (reflux).

The mixture is stirred for a further 15 minutes and a further 232 kg of chlorine are then passed in, at a vigorous reflux, in accordance with the following program:

1st hour: 40 kg of chlorine
2nd hour: 80 kg of chlorine
3rd hour: 80 kg of chlorine
4th hour: 32 kg of chlorine (vigorous evolution of HCl).

The mixture is then stirred for a further hour at 115° C. and the phosphorus oxychloride is then removed by distillation through a short column, first under normal pressure and finally under an increasing vacuum.

2-Chlorobenzthiazole is then distilled off under 20 mbar and at top temperatures of 122°-125° C.

478 kg of a main fraction containing 97.8% of 2-chlorobenzthiazole are obtained, which corresponds to a yield of 91.9% of theory.

The distillation residue, about 43 kg, is readily soluble in 1,2-dichlorobenzene.

Example 3

10 g of chlorine are passed into a mixture of 585 ml of chlorobenzene, 270 g (2 mols) of benzthiazole, 2 g of iron-III chloride and 7 g of phosphorus trichloride at 100° C.

A further 140 g of chlorine are then passed in at reflux temperature in the course of 5-6 hours—initially quite slowly and later rapidly.

The evolution of gas is complete after stirring for a further hour.

The following were obtained after working up by vacuum distillation in a customary manner:

624 g of chlorobenzene (containing 1.1% of benzthiazole and 2.1% of 2-chlorobenzthiazole) 312 g of main fraction (0.8% of chlorobenzene), 98.6% of 2-chlorobenzthiazole and 0.7% unknown) and 29 g of distillation residue.

Yield of 2-chlorobenzthiazole; 95.0% of theory, relative to charge; (97.5% of theory, relative to conversion).

If only 450 ml of chlorobenzene are used instead of 585 ml, a yield of only 90.1% of theory is obtained; if only 360 ml are used the yield of 2-chlorobenzthiazole is only 71.7% of theory.

An equimolar amount of aluminum chloride can be used with virtually identical results instead of iron-III chloride.

It will be understood that the specification and examples are illustrative but not limitative of the present invention and that other embodiments within the spirit and scope of the invention will suggest themselves to those skilled in the art.

What is claimed is:

1. In the preparation of 2-chlorobenzthiazole by reacting benzthiazole with elementary chlorine in an inert solvent in the presence of a catalyst at elevated temperature, the improvement wherein the solvent is phosphorus oxychloride or chlorobenzene and is maintained in boiling condition during the reaction.

2. A process according to claim 1, wherein the catalyst is iron-III chloride or aluminum chloride.

3. A process according to claim 1, wherein phosphorus trichloride or pyridine is also present as a co-catalyst.

4. A process according to claim 1, wherein the solvent is phosphorus oxychloride and it is present in about 180 to 300 ml per mol of benzthiazole.

5. A process according to claim 1, wherein the solvent is chlorobenzene and it is present in about 200 to 350 ml per mol of benzthiazole.

6. A process according to claim 1, wherein the catalyst is iron-III chloride or aluminum chloride and phosphorus trichloride or pyridine is also present as a co-catalyst.

* * * * *